United States Patent [19]

Takahashi et al.

[11] Patent Number: 4,539,355
[45] Date of Patent: Sep. 3, 1985

[54] PHOSPHORUS-CONTAINING COMPOUNDS, THEIR PRODUCTION AND THEIR USE AS ANTIOXIDANTS

[75] Inventors: Yukoh Takahashi; Shinichi Yachigo, both of Toyonaka; Tamaki Ishii, Suita, all of Japan

[73] Assignee: Sumitomo Chemical Company, Limited, Osaka, Japan

[21] Appl. No.: 504,782

[22] Filed: Jun. 16, 1983

[30] Foreign Application Priority Data

Jun. 23, 1982 [JP] Japan ................................ 57-108714
Mar. 14, 1983 [JP] Japan ................................ 58-42868

[51] Int. Cl.³ .......................... C07F 9/36; C08K 5/53
[52] U.S. Cl. .................................... 524/131; 260/941
[58] Field of Search ...................... 260/941; 524/131; 560/130; 528/287

[56] References Cited

U.S. PATENT DOCUMENTS

| | | | |
|---|---|---|---|
| 1,869,657 | 8/1932 | Bowers | 260/809 |
| 2,754,320 | 7/1956 | Johnston | 260/941 |
| 3,180,847 | 4/1965 | Fowler et al. | 524/135 |
| 3,539,531 | 11/1970 | Drake et al. | 524/130 |
| 3,717,611 | 2/1973 | Baumer et al. | 560/130 |
| 3,784,652 | 1/1974 | Gourse | 524/130 |
| 3,809,676 | 5/1974 | Liberti | 524/133 |
| 4,254,018 | 3/1981 | Kowallik et al. | 524/131 |

FOREIGN PATENT DOCUMENTS 51-95494  8/1976  Japan .
58-99491  6/1983  Japan .

*Primary Examiner*—Veronica P. Hoke
*Attorney, Agent, or Firm*—Wenderoth, Lind & Ponack

[57] ABSTRACT

Phosphorus-containing compounds of the formula:

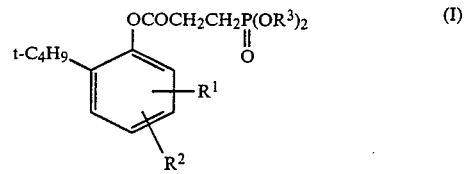

(I)

wherein $R^1$ and $R^2$ are each a hydrogen atom or a lower alkyl group, and $R^3$ is a lower alkyl or phenyl group. These compounds may be used as stabilizers against the action of heat, light and oxygen for organic substances and especially polyolefin resins. These phosphorus-containing compounds may be used in conjunction with other stabilizers such phenol-type and sulfur-containing antioxidants, especially in polyolefin resin compositions to produce a polyolefin resin composition having excellent resistance to light, heat and oxygen. The present invention also relates to a method of producing the compounds of the aforementioned formula by reacting

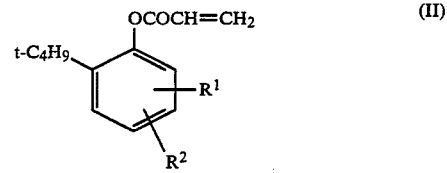
(II)

with a disubstituted phosphonate of the formula

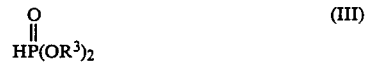
(III)

wherein $R^1$, $R^2$ and $R^3$ are as defined above.

7 Claims, No Drawings

PHOSPHORUS-CONTAINING COMPOUNDS, THEIR PRODUCTION AND THEIR USE AS ANTIOXIDANTS

The present invention relates to novel phosphorus-containing compounds, their production and their use as an antioxidant.

It is conventionally well known that various organic substances described below are subject to deterioration by heat, light and oxygen: Synthetic resins such as polyolefin, ABS resins, polystyrene, high impact polystyrene, acrylonitrile/styrene compolymers, polyamides, polyacetals, ethylene/propylene copolymers, etc.; natural rubbers; synthetic rubbers such as butadiene rubber, isoprene rubber, isoprene/isobutylene copolymer rubber, styrene/butadiene copolymer rubber, acrylonitrile/butadiene copolymer rubber, ethylene/propylene copolymer rubber, etc.; petroleum products such as lubricating oil, fuel oil, etc.; and oil and fat, grease and the like.

Particularly, polyolefin resins such as polyethylene, polypropylene, etc. have excellent physical, chemical and electrical properties, so that they are formed into molded products, pipe, sheet, film, etc. by various methods such as blow molding, extrusion molding, injection molding, calendering and the like, and used in many fields. It is, however, well known that polyolefin resins, when used alone, deteriorate on processing or use, by the action of heat, light, oxygen, etc., thereby showing a remarkable reduction in physical property followed by phenomena such as softening, brittleness, discoloration and the like.

For the purpose of preventing such phenomena, to use antioxidants is conventionally well known. Such antioxidants include for example phosphorus-containing antioxidants such as distearyl pentaerythritol diphosphite, tris(2,4-di-tert-butylphenyl)phosphite, tris(2-tert-butyl-4-methylphenyl)phosphite, bis (2,4-di-tert-butylphenyl)pentaerythritol diphosphite, tetrakis(2,4-di-tert-butylphenyl)-4,4'-biphenylene diphosphite, etc.; phenol-type antioxidants such as 2,6-di-tert-butyl-4-methylphenol, n-octadecyl β-(3,5-di-tert-butyl-4-hydroxyphenyl)propionate, tetrakis[methylene-3-(3,5-di-tert-butyl-4-hydroxyphenyl)propionate]methane, 1,3,5-trimethyl-2,4,6-tris(3,5-di-tert-butyl-4-hydroxybenzyl)benzene, 1,1,3-tris(2-methyl-4-hydroxy-5-tert-butylphenyl)butane, tris(2,6-dimethyl-4-tert-butyl-3-hydroxybenzyl)isocyanulate, etc.; and sulfur-containing antioxidants such as dilauryl thiodipropionate, dimyristyl thiodipropionate, distearyl thiodipropionate, pentaerythritol tetrakis(β-dodecylthiopropionate), etc. But, these compounds have defects in that, when they are kept in organic substances at high temperatures for long periods of time, their effects have a short durability. For example, of polyolefin resins are used in combination with these antioxidants, they were not sufficient in an effect to prevent deterioration by heat, oxidation, etc., and particularly unsatisfactory in a discoloration-preventing effect.

In view of this situation the present inventors have extensively studied to overcome these defects and develop compounds having improved superior deterioration-preventing performances, and as a result, succeeded in developing a phosphorus-containing compound represented by the formula (I),

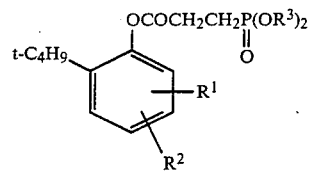

wherein $R^1$ and $R^2$ are each a hydrogen atom or a lower alkyl group, and $R^3$ is a lower alkyl or phenyl group, and found that said compound is very useful as a deterioration-preventing agent.

The phosphorus-containing compound represented by the abovementioned formula (I) is a novel compound first synthesized by the present inventors, and said compound can be produced by reacting a phenol monoacrylate represented by the formula (II),

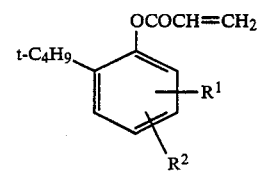

wherein $R^1$ and $R^2$ have the same meanings as above, with a disubstituted phosphonate represented by the formula (III),

wherein $R^3$ has the same meaning as above.

As the lower alkyl group in substituents $R^1$, $R^2$ and $R^3$, there are given for example methyl, ethyl, n-propyl, isopropyl, n-butyl, tert-butyl and the like.

In producing the phosphorus-containing compound of the present invention represented by the formula (I), phenol monoacrylate, a starting material, represented by the formula (II) is a novel compound. This compound can be produced, for example, by reacting 2-tert-butyl-4-methylphenol, 2-tert-butyl-6-methylphenol, 2-tert-butyl-5-methylphenol, 2-tert-butyl-4,6-dimethylphenol or the like with acryloyl chloride in an inert solvent (e.g. toluene) in the presence of a dehydrochlorinating agent such as triethylamine, pyridine or the like. Disubstituted phosphonates, the other starting material, represented by the formula (III) are well-known compounds. Specifically, the compounds include for example dimethyl phosphonate, diethyl phosphonate, di-n-propyl phosphonate, diisopropyl phosphonate, di-n-butyl phosphonate, diphenyl phosphonate and the like.

This reaction between phenol monoacrylate and disubstituted phosphonate is carried out in a solvent in the presence of, generally, a basic catalyst.

As the solvent used in this reaction, alcohols (e.g. methanol, ethanol, tert-butyl alcohol), ethers (e.g. ethylene glycol dimethyl ether, dioxane, tetrahydrofuran), halogenated hydrocarbons (e.g. dichloromethane, chloroform) and the like are used. Of these, chloroform is particularly preferred.

As the basic catalyst, alkali metal hydroxides (e.g. sodium hydroxide, potassium hydroxide), alkali metal alkoxides (e.g. sodium methoxide, sodium ethoxide, potassium tert-butoxide), tertiary amines (e.g. triethylamine), benzyltrimethylammonium hydroxide and the like are used. Of these, sodium methoxide is particularly preferred. The amount of the catalyst used is within a range of, generally, 0.01 to 20 mole%, preferably 0.1 to 10 mole%, based on 1 mole of phenol monoacrylate.

The reaction temperature is within a range of 0° C. to the refluxing temperature of the solvent used, but generally, it is the refluxing temperature.

The molar ratio of both starting materials in the reaction of this method is generally 0.9 to 1.1, as expressed in the ratio of phenol monoacrylate to disubstituted phosphonate.

As a method to separate the product in this reaction, there is one in which, after completion of the reaction, the reaction solution is cooled to about 40° C. or less, the basic catalyst in it is neutralized with an acid, and after washing the solution with water, the solvent is removed from the organic layer by evaporation. By this method, a product having a purity of not less than 95% is obtained, but the product may be purified by recrystallization or the like if necessary.

As the phosphorus-containing compound (phosphonates) represented by the formula (I) of the present invention thus produced, the following compounds are specifically given:

Dimethyl 2-tert-butyl-4-methylphenoxycarbonylethyl phosphonate,
dimethyl 2-tert-butyl-5-methylphenoxycarbonylethyl phosphonate,
dimethyl 2-tert-butyl-4,6-dimethylphenoxycarbonylethyl phosphonate,
diethyl 2-tert-butyl-4-methylphenoxycarbonylethyl phosphonate,
diethyl 2-tert-butyl-5-methylphenoxycarbonylethyl phosphonate,
diethyl 2-tert-butyl-4,6-dimethylphenoxycarbonylethyl phosphonate,
dipropyl 2-tert-butyl-4-methylphenoxycarbonylethyl phosphonate,
dipropyl 2-tert-butyl-5-methylphenoxycarbonylethyl phosphonate,
dipropyl 2-tert-butyl-4,6-dimethylphenoxycarbonylethyl phosphonate,
diisopropyl 2-tert-butyl-4-methylphenoxycarbonylethyl phosphonate,
diisopropyl 2-tert-butyl-5-methylphenoxycarbonylethyl phosphonate,
diisopropyl 2-tert-butyl-4,6-dimethylphenoxycarbonylethyl phosphonate,
dibutyl 2-tert-butyl-4-methylphenoxycarbonylethyl phosphonate,
dibutyl 2-tert-butyl-5-methylphenoxycarbonylethyl phosphonate,
dibutyl 2-tert-butyl-4,6-dimethylphenoxycarbonylethyl phosphonate,
diphenyl 2-tert-butyl-4-methylphenoxycarbonylethyl phosphonate,
diphenyl 2-tert-butyl-5-methylphenoxycarbonylethyl phosphonate,
diphenyl 2-tert-butyl-4,6-dimethylphenoxycarbonylethyl phosphonate, and the like.

These novel phosphorus-containing compounds of the present invention are useful not only as a deterioration-preventing agent for various organic substances but also, particularly, as a color-improving agent.

The phosphorus-containing antioxidants of the present invention are particularly useful as a stabilizer for polyolefin resins. That is, the present inventors found that by blending polyolefin resins with, as a phosphorus-containing antioxidant, a specified amount of phosphonate represented by the above-mentioned formula (I) and specified amounts of the conventionally well-known phenol-type antioxidants or/and sulfur-containing ones a very superior synergistic effect that can never be expected from the combination of the well-known antioxidants is obtained, whereby polyolefin resin compositions are obtained which are stable to deterioration by heat and oxidation as well as very stable to discoloration.

The present invention provides a stabilized polyolefin resin composition characterized in that said composition contains a phosphorus-containing, phenol-type and sulfur-containing antioxidants in amounts of 0.01 to 5 parts by weight, 0.005 to 2 parts by weight and 0 to 5 parts by weight, respectively, based on 100 parts by weight of polyolefin resin, and that said phosphorus-containing antioxidant is a phosphonate represented by the above-mentioned formula (I).

The phenol-type antioxidant and sulfur-containing one used in the present invention are well-known compounds previously given as an antioxidants, and they are not particularly limited.

The polyolefin resin composition of the present invention comprises a polyolefin resin and the foregoing antioxidants, i.e. phosphonates represented by the formula (I) and a phenol-type and sulfur-containing antioxidants. The contents of these antioxidants based on 100 parts by weight of polyolefin resin are 0.01 to 5 parts by weight, preferably 0.1 to 2 parts by weight for phosphonate, 0.005 to 2 parts by weight, preferably 0.01 to 0.5 part by weight for the phenol-type antioxidant, and 0 to 5 parts by weight for the sulfur-containing one. Hereupon, to use the sulfur-containing antioxidant together is not always necessary when the prevention of discoloration is a primary object, but it is very useful when the prevention of deterioration also is intended at the same time. When said antioxidant is used together, its content is 0.01 to 5 parts by weight, preferably 0.1 to 2 parts by weight based on 100 parts by weight of polyolefin resin.

The polyolefin resin composition of the present invention is obtained by blending a polyolefin resin with the above-mentioned stabilizing component of the present invention. As a method of blending, the conventionally well-known equipments and methods for mixing and blending polyolefin resins with stabilizers, pigments, fillers and the like may be applied.

The polyolefin resin composition of the present invention may contain other additives according to its objects and uses. As the additives, there may be given for example antioxidants other than those used in the present invention, UV absorbers, photostabilizers, metal sequestering agents, metal soaps, nucleating agents, lubricants, antistatic agents, flame retardants, pigments, fillers and the like. For example, the lightfastness of the composition can be improved by adding UV absorbers and photostabilizers such as 2-hydroxy-4-methoxybenzophenone, 2-hydroxy-4-n-octoxybenzophenone, 2-(2-hydroxy-5-methylphenyl)benzotriazole, 2-(2-hydroxy-3-tert-butyl-5-methylphenyl)-5-chlorobenzotriazole, 2-(2-hydroxy-3,5-di-tert-butylphenyl)-5-chlorobenzotriazole, 2-(2-hydroxy-3,5-di-amylphenyl)benzotriazole, nickel salt of [2,2'-thiobis(4-tert-octylphenolate)]butylamine, 2,2,6,6-tetramethyl-4-piperidinyl benzoate, bis(2,2,6,6-tetramethyl-4-piperidinyl)sebacate, 2-(3,5-ditert-butyl-4-hydroxybenzyl)-2-n-butylmalonic acid, bis(1,2,2,6,6-pentamethyl-4-piperidyl), 1-[2-{3-(3,5-di-tert-butyl-4-hydroxyphenyl)propionyloxy}ethyl]-4-[3-(3,5-di-tert-butyl-4-hydroxyphenyl)propionyloxy]-2,2,6,6-tetramethylpiperidine, polycondensation products of dimethyl succinate and 1-(2-hydroxyethyl)-4-hydroxy-2,2,6,6-tetramethylpiperidine, and the like.

As the polyolefin resin used in the present invention, there may be used poly-α-olefins such as low-density polyethylene, medium- to high-density polyethylene, linear low-density polyethylene, polypropylene, polybutene-1, etc.; poly-α-olefin copolymers such as propylene/ethylene random or block copolymer, ethylene/butene-1 random copolymer, etc.; poly-α-olefin/vinyl monomer copolymers such as maleic anhydride-modified polypropylene; and mixtures thereof. Particularly, polypropylene is preferred.

Next, the present invention will be illustrated in detail with reference to the following examples, which are not however to be interpreted as limting the invention thereto.

Material-production example 1

To a 300-ml four-necked flask equipped with a thermometer, a stirrer, a condenser and a dropping funnel were added 32.8 g (0.20 mole) of 2-tert-butyl-4-methylphenol, 22.3 g (0.22 mole) of triethylamine and 100 g of toluene, and after replacing air in the flask by nitrogen, 19.10 g (0.21 mole) of acryloyl chloride was added dropwise at a reaction temperature of 30° C. over 1 hour. After completion of the dropwise addition, excessive triethylamine was neutralized with hydrochloric acid, the reaction solution was washed with water, and toluene was then removed from the organic layer by evaporation under reduced pressure to obtain 43.0 g of a crude product (yield, 99%). This crude product was purified by distillation under reduced pressure to obtain a white and transparent 2-tert-butyl-4-methylphenol monoacrylate.

Melting point 54°–56° C.; Boiling point 120°–122° C./4 mmHg.

Material-production example 2

2-tert-Butyl-5-methylphenol monoacrylate was obtained by carrying out reaction under the same condition as in Material-production example 1 except that 2-tert-butyl-5-methylphenol was used as a starting material.

Boiling point 95°–98° C./1 mmHg (oily product)

Material-production example 3

2-tert-Butyl-4,6-dimethylphenol monoacrylate was obtained by carrying out reaction under the same condition as in Material-production example 1 except that 2-tert-butyl-4,6-dimethylphenol was used as a starting material.

Melting point 53°–55° C. (white crystal) Boiling point 93°–95° C./1 mmHg

EXAMPLE 1

To a 200-ml four-necked flask equipped with a thermometer, a stirrer and a condenser were added 6.80 g (0.031 mole) of 2-tert-butyl-4-methylphenol monoacrylate, 4.30 g (0.031 mole) of diethyl phosphonate and 50 g of chloroform. After replacing air in the flask by nitrogen, 0.16 g (0.0008 mole) of a 28 wt.% methanol solution of sodium methoxide was added, and the mixture was kept at 61° C. for 8 hours. After completion of the reaction, the reaction solution was cooled to not more than 40° C., neutralized with a dilute hydrochloric acid and washed with water, and chloroform was then removed from the organic layer by evaporation under reduced pressure. The residue was recrystallized from n-hexane to obtain 10.4 g of a white crystalline diethyl 2-tert-butyl-4-methylphenoxycarbonylethyl phosphonate (yield, 90%).

Melting point 52°–54° C.

Elementary analysis (as $C_{13}H_{29}O_5P$): C: 60.80% (60.66%); H: 8.10% (8.20%); P: 8.59% (8.69%).

Values in the parenthesis are a calculated value.

Infrared absorption spectrum (liquid paraffin method; unit, $cm^{-1}$):

1745($\nu$c=o), 1630($\nu$arom c=c), 1240($\nu$c-o), 1190, out of plane 1150, 1018($\nu$p-o), 805($\delta$arom C-H)

EXAMPLE 2

Reaction was carried out under the same condition as in Example 1 except that 2-tert-butyl-4-methylphenol monoacrylate and diphenyl phosphonate were used as a starting material. Thus, diphenyl 2-tert-butyl-4-methylphenoxycarbonylethyl phosphonate was obtained as a colorless, transparent and viscous substance.

Elementary analysis (as $C_{26}H_{29}PO_5$): C: 69.05% (69.02%); H: 6.52% (6.46%); P: 6.60% (6.85%).

Values in the parenthesis are a calculated value.

Infrared absorption spectrum (liquid paraffin method; unit, $cm^{-1}$):

1740($\nu$c=o), 1610($\nu$arom c=c), 1230($\nu$c-o), 1190, 1140, out of plane 1020($\nu$p-o), 820($\delta$arom C-H).

EXAMPLE 3

To the same flask as used in Example 1 were added 6.80 g (0.031 mole) of 2-tert-butyl-5-methylphenol monoacrylate, 7.26 g (0.031 mole) of diphenyl phosphonate and 50 g of chloroform. After replacing air in the flask by nitrogen, 0.10 g (0.0005 mole) of a 28 wt.% methanol solution of sodium methoxide was added, and the mixture was kept at 61° C. for 10 hours. After completion of the reaction, the reaction solution was cooled to 40° C., neutralized with a dilute hydrochloric acid and washed with water, and chloroform was then removed from the organic layer by evaporation under reduced pressure. Thus, 13.61 g of diphenyl 2-tert-butyl-5-methylphenoxycarbonylethyl phosphonate was obtained as a colorless, transparent and viscous substance (yield, 97%).

Elementary analysis (as $C_{26}H_{29}O_5P$): C: 68.95% (69.02%); H: 6.60% (6.46%); P: 6.92% (6.85%).

Values in the parenthesis are a calculated value.

Infrared absorption spectrum (liquid paraffin method; unit, $cm^{-1}$):

1750($\nu$c=o), 1620($\nu$arom c=c), 1245($\nu$c-o), 1180, 1140, out of plane 1020($\nu$p-o), 795($\delta$arom C-H).

EXAMPLE 4

To the same flask as used in Example 1 were added 7.0 g (0.030 mole) of 2-tert-butyl-4,6-dimethylphenol monoacrylate, 5.83 g (0.030 mole) of dibutyl phosphonate and 50 g of chloroform. After replacing air in the flask by nitrogen, 0.15 g (0.00078 mole) of a 28 wt.% methanol solution of sodium methoxide was added, and the mixture was kept at 61° C. for 8 hours. After completion of the reaction, the reaction solution was cooled to not more than 40° C., neutralized with a dilute hydrochloric acid and washed with water, and chloroform was then removed from the organic layer by evaporation under reduced pressure. The residue was recrystallized from n-hexane to obtain 11.0 g of dibutyl 2-tert-butyl-4,6-dimethylphenoxycarbonylethyl phosphonate as a white crystal (yield, 86%).

Melting point 62°–63° C.

Elementary analysis (as $C_{23}H_{39}O_5P$): C: 64.85% (64.77%); H: 9.16% (9.22%); P: 7.10% (7.26%).

Values in the parenthesis are a calculated value.

Infrared absorption spectrum (liquid paraffin method; unit $cm^{-1}$):

1755($\nu c=o$), 1620($\nu arom\ c-H$), 1250($\nu c-o$), 1150, out of plane 1030($\nu p-o$), 840($\delta arom\ c-H$).

EXAMPLE 5

The blend described below was well mixed on a mixer for 5 minutes and kneaded on a mixing roll of 180° C. to obtain a compound. The compound was formed into a sheet of 1 mm in thickness on a hot press of 210° C. to prepare a test piece of 40×40×1 mm in size. The test piece was heat-deteriorated in a Geer oven of 100° C. for a definite period of time, and the degree of discoloration was judged by means of the yellow index value (ΔYI) of a color-difference meter. The result is shown in Table 1.

| Compounding: | Part by weight |
|---|---|
| Unstabilized polypropylene resin | 100 |
| Calcium stearate | 0.1 |
| 2,6-Di-tert-butyl-p-cresol | 0.2 |
| Phosphorus-containing compound to be tested | 0.2 |

TABLE 1

| | No. | Phosphorus-containing compound to be tested | 0 | ΔYI value 25 hours | 50 hours |
|---|---|---|---|---|---|
| Example | 1 | Compound in Example 1 | −2.6 | 1.3 | 4.2 |
| | 2 | Compound in Example 2 | −2.0 | 2.5 | 5.5 |
| | 3 | Compound in Example 3 | −1.8 | 2.7 | 5.9 |
| | 4 | Compound in Example 4 | −2.5 | 1.8 | 4.6 |
| Comparative example | 5 | Trisnonylphenyl phosphite | −1.0 | 6.7 | 10.6 |
| | 6 | No addition | Control | 30.6 | 59.5 |

EXAMPLE 6

The blend described below was well mixed on a mixer for 5 minutes and kneaded on a mixing roll of 180° C. to obtain a compound. The compound was formed into a sheet of 1 mm in thickness on a hot press of 210° C. to prepare a test piece of 40×40×1 mm in size. The test piece was placed in a Geer oven of 160° C., and a period of time which had passed until 30% of the area of the test piece showed brittleness was measured. The thermal stability and oxidation stability were evaluated with said period of time as a induction period for heat embrittlement. Further, the degree of discoloration was judged by means of the yellow index value (ΔYI) of a color-difference meter.

The result is shown in Table 2.

| Compounding: | Part by weight |
|---|---|
| Unstabilized polypropylene resin | 100 |
| Calcium stearate | 0.1 |
| Test compound | varying amount |

The symbols of test compund in Table 2 mean the following compounds.

1-1: Diethyl 2-tert-butyl-4-methylphenoxycarbonylethyl phosphonate
1-2: Diphenyl 2-tert-butyl-4-methylphenoxycarbonylethyl phosphonate
1-3: Diphenyl 2-tert-butyl-5-methylphenoxycarbonylethyl phosphonate
1-4: Dibutyl 2-tert-butyl-4,6-dimethylphenoxycarbonylethyl phosphonate
AO-1: Distearyl pentaerythritol diphosphite
AO-2: Tetrakis(2,4-di-tert-butylphenyl)-4,4'-biphenylene diphosphite
AO-3: Tetrakis[methylene-3-(3,5-di-tert-butyl-4-hydroxyphenyl)propionate]methane
AO-4: Dilauryl thiodipropionate
AO-5: Pentaerythritol tetrakis(β-dodecylthiopropionate)

TABLE 2

| Test compound | | Example 1 | 2 | 3 | 4 | 5 | 6 | 7 | 8 | Comparative example 9 | 10 | 11 | 12 | 13 | 14 | 15 |
|---|---|---|---|---|---|---|---|---|---|---|---|---|---|---|---|---|
| Phosphorus-containing compound | 1-1 | 0.2 | 0.2 | | | | | | | | | | | | | No addition |
| | 1-2 | | | 0.2 | 0.2 | | | | | | | | | | | |
| | 1-3 | | | | | 0.2 | 0.2 | | | | | | | | | |
| | 1-4 | | | | | | | 0.2 | 0.2 | | | | | | | |
| | AO-1 | | | | | | | | | | | 0.2 | 0.2 | | | |
| | AO-2 | | | | | | | | | | | | | 0.2 | 0.2 | |
| Phenol-type compound | AO-3 | 0.05 | 0.05 | 0.05 | 0.5 | 0.5 | 0.5 | 0.5 | 0.5 | 0.5 | 0.5 | 0.5 | 0.5 | 0.5 | 0.5 | |
| Sulfur-containing compound | AO-4 | 0.2 | | 0.2 | | 0.2 | | 0.2 | | 0.2 | | 0.2 | | 0.2 | | |
| | AO-5 | | 0.2 | | 0.2 | | 0.2 | | 0.2 | | 0.2 | | 0.2 | | 0.2 | |
| Induction period for heat embrittlement (hr) | | 630 | 600 | 615 | 590 | 610 | 590 | 625 | 605 | 450 | 400 | 470 | 415 | 480 | 420 | 5 |
| Degree of discoloration ΔYI value | Before ageing | −8.0 | −7.5 | −7.6 | −7.0 | −7.3 | −6.8 | −8.0 | −7.4 | 0.3 | 0.7 | −1.4 | −0.1 | −2.1 | −3.0 | Control |
| | 48 hours' ageing | −17.6 | −18.0 | −17.2 | −17.5 | −16.9 | −17.0 | −17.4 | −17.7 | −7.2 | −8.8 | −11.7 | −11.3 | −8.9 | −10.3 | — |
| | 96 hours' ageing | −14.4 | −15.2 | −14.0 | −14.3 | −13.7 | −14.1 | −14.3 | −14.9 | 1.2 | −2.8 | −5.2 | −6.4 | −1.3 | −4.0 | — |

TABLE 2-continued

| Test compound | Example No. 1 | 2 | 3 | 4 | 5 | 6 | 7 | 8 | Comparative example No. 9 | 10 | 11 | 12 | 13 | 14 | 15 |
| --- | --- | --- | --- | --- | --- | --- | --- | --- | --- | --- | --- | --- | --- | --- | --- |
| ageing | | | | | | | | | | | | | | | |

EXAMPLE 7

Polypropylene resin compositions were obtained in the same manner as in Example 6 except that the compounds in Table 3 were used as a test compound. Test pieces were prepared, and using them, the thermal stability, oxidation stability and degree of discoloration were similarly evaluated. The result is shown in Table 3.

dimethylphenoxycarbonylethyl phosphonate, dibutyl 2-tert-butyl-4-methylphenoxycarbonylethyl phosphonate, dibutyl 2-tert-butyl-5-methylphenoxycarbonylethyl phosphonate, dibutyl 2-tert-butyl-4,6-dimethylphenoxycarbonylethyl phosphonate, diphenyl 2-tert-butyl-4-methylphenoxycarbonylethyl phosphonate, diphenyl 2-tert-butyl-5-methylphenoxycarbonylethyl phosphonate and diphenyl 2-tert-butyl-4,6-dimethylphenoxycarbonylethyl phosphonate.

TABLE 3

| Test compound | | Example No. 1 | 2 | 3 | 4 | 5 | 6 | 7 | Comparative example 8 |
| --- | --- | --- | --- | --- | --- | --- | --- | --- | --- |
| Phosphorus- | 1-1 | 0.2 | | | | | | | No |
| containing | 1-2 | | 0.2 | | | | | | addi- |
| compound | 1-3 | | | 0.2 | | | | | tion |
| | 1-4 | | | | 0.2 | | | | |
| | AO-1 | | | | | | 0.2 | | |
| | AO-2 | | | | | | | 0.2 | |
| Phenol-type compound | AO-3 | 0.05 | 0.05 | 0.05 | 0.05 | 0.05 | 0.05 | 0.05 | |
| Induction period for heat embrittlement (hr) | | 180 | 160 | 155 | 175 | 85 | 120 | 115 | 5 |
| Degree of discoloration ΔYI value | Before ageing | −11.2 | −10.2 | −9.7 | −10.9 | −1.3 | −3.7 | −4.0 | Control |
| | 24 hours' ageing | −16.8 | −15.5 | −14.9 | −16.1 | −6.2 | −10.1 | −9.0 | — |
| | 72 hours' ageing | −13.7 | −12.6 | −12.3 | −12.2 | 14.2 | 7.3 | 8.6 | — |

What is claimed is:

1. A phosphorus-containing compound represented by the formula (1),

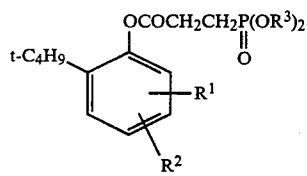

$$\text{(I)}$$

wherein $R^1$ and $R^2$ are each a hydrogen atom or a lower alkyl group, and $R^3$ is a lower alkyl or phenyl group.

2. A phosphorus-containing compound as described in claim 1 selected from the group consisting of dimethyl 2-tert-butyl-4-methylphenoxycarbonylethyl phosphonate, dimethyl 2-tert-butyl-5-methylphenoxycarbonylethyl phosphonate, dimethyl 2-tert-butyl-4,6-dimethylphenoxycarbonylethyl phosphonate, diethyl 2-tert-butyl-4-methylphenoxycarbonylethyl phosphonate, diethyl 2-tert-butyl-5-methylphenoxycarbonylethyl phosphonate, diethyl 2-tert-butyl-4,6-dimethylphenoxycarbonylethyl phosphonate, dipropyl 2-tert-butyl-4-methylphenoxycarbonylethyl phosphonate, dipropyl 2-tert-butyl-5-methylphenoxycarbonylethyl phosphonate, dipropyl 2-tert-butyl-4,6-dimethylphenoxycarbonylethyl phosphonate, diisopropyl 2-tert-butyl-4-methylphenoxycarbonylethyl phosphonate, diisopropyl 2-tert-butyl-5-methylphenoxycarbonylethyl phosphonate, diisopropyl 2-tert-butyl-4,6-dimethylphenoxycarbonylethyl phosphonate, dibutyl 2-tert-butyl-4-methylphenoxycarbonylethyl phosphonate, dibutyl 2-tert-butyl-5-methylphenoxycarbonylethyl phosphonate, dibutyl 2-tert-butyl-4,6-dimethylphenoxycarbonylethyl phosphonate, diphenyl 2-tert-butyl-4-methylphenoxycarbonylethyl phosphonate, diphenyl 2-tert-butyl-5-methylphenoxycarbonylethyl phosphonate and diphenyl 2-tert-butyl-4,6-dimethylphenoxycarbonylethyl phosphonate.

3. A method of stabilizing an organic resin subject to deterioration by heat, light or oxygen, by adding to said organic resin, a stabilizing amount of the phosphorus-containing compound of claim 1.

4. A polyolefin resin composition characterized in that said composition contains phosphorus-containing, phenol-type and sulfur-containing antioxidants in amounts of 0.01 to 5 parts by weight, 0.005 to 2 parts by weight and 0 to 5 parts by weight, respectively, based on 100 parts by weight of polyolefin resin, and said phosphorus-containing antioxidant is a phosphonate represented by the formula (I),

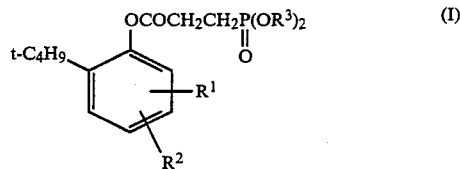

$$\text{(I)}$$

wherein $R^1$ and $R^2$ are each a hydrogen atom or a lower alkyl group, and $R^3$ is a lower alkyl or phenyl group.

5. A polyolefin resin composition as described in claim 4, wherein said polyolefin resin is polypropylene.

6. A method according to claim 3 wherein the organic resin is a polyolefin resin.

7. A method according to claim 6 wherein the polyolefin resin is polypropylene.

* * * * *